(12) United States Patent
Penhasi

(10) Patent No.: US 10,064,829 B2
(45) Date of Patent: Sep. 4, 2018

(54) PROBIOTIC LIQUID FOOD PRODUCTS FOR INFANTS

(71) Applicants: DEGAMA SMART LTD., Grand Cayman (KY); Adel Penhasi, Holon (IL)

(72) Inventor: Adel Penhasi, Holon (IL)

(73) Assignee: DeGama Smart, Ltd., Grand Cayman (KY)

( * ) Notice: Subject to any disclaimer, the term of this patent is extended or adjusted under 35 U.S.C. 154(b) by 6 days.

(21) Appl. No.: 14/785,604

(22) PCT Filed: Apr. 19, 2014

(86) PCT No.: PCT/IL2014/050368
§ 371 (c)(1),
(2) Date: Oct. 19, 2015

(87) PCT Pub. No.: WO2014/170904
PCT Pub. Date: Oct. 23, 2014

(65) Prior Publication Data
US 2016/0081940 A1    Mar. 24, 2016

Related U.S. Application Data

(60) Provisional application No. 61/813,663, filed on Apr. 19, 2013.

(51) Int. Cl.
*A61K 35/741* (2015.01)
*A61K 9/16* (2006.01)
*A61K 9/50* (2006.01)
*C12N 1/20* (2006.01)
*A61K 9/00* (2006.01)
*A23P 10/20* (2016.01)
*A23L 33/00* (2016.01)
*A23L 33/135* (2016.01)

(52) U.S. Cl.
CPC .......... *A61K 9/5036* (2013.01); *A23L 33/135* (2016.08); *A23L 33/40* (2016.08); *A23P 10/20* (2016.08); *A61K 9/0095* (2013.01); *A61K 9/5073* (2013.01); *A61K 35/741* (2013.01); *C12N 1/20* (2013.01); *A23V 2002/00* (2013.01)

(58) Field of Classification Search
None
See application file for complete search history.

(56) References Cited

FOREIGN PATENT DOCUMENTS

| WO | WO 2009158368 | * | 12/2009 |
|---|---|---|---|
| WO | WO 2012020403 | * | 2/2012 |

\* cited by examiner

*Primary Examiner* — Alton N Pryor
(74) *Attorney, Agent, or Firm* — Strategy IP, a PLC

(57) ABSTRACT

Provided are heat-processed or heat-processible health food products beneficially affecting the consumer's intestinal microbial balance. The food products are particularly liquid-based products which comprise a probiotic component capable of resisting heat and humidity.

11 Claims, 9 Drawing Sheets

PROBIOTIC LIQUID FOOD PRODUCTS FOR INFANTS

FIELD OF THE INVENTION

The present invention relates to health food products, particularly, to liquid products containing probiotics for infants.

BACKGROUND OF THE INVENTION

Probiotics are live microbial food supplements which beneficially affect the host by supporting naturally occurring gut flora, by competing harmful microorganisms in the gastrointestinal tract, by assisting useful metabolic processes, and by strengthening the resistance of the host organism against toxic substances. A number of organisms is used in probiotic foods, an example being bacterial genera *Lactobacillus* or *Bifidobacterium*, or *Lactobacillus paracasei* St11 (or NCC2461), *Lactobacillus fortis*, *Lactobacillus johnsonii* Lα1 (=*Lactobacillus* LC1, *Lactobacillus johnsonii* NCC533) or *Bifidobacterium lactis*. Probiotic organisms should survive for the lifetime of the product in order to be effective, and further they should survive the whole way through the gastrointestinal tract to the colon. Probiotic organisms are usually incorporated into milk products, such as yogurts. The need is felt to deliver the beneficial microorganisms in other foodstuff types, for example in liquid-based products especially those which undergo heat treatment in at least one stage of their preparation. The main problem in preparing liquid-based health food is the combination of high temperature and water that may destroy the whole, or a significant portion, of the included probiotics.

US 2005/0019417 A1 describes a method of preparing products containing moisture-sensitive living microorganisms including probiotics, comprising at least the steps through which a suspension of probiotics and a sugar polymer in water miscible solvent is sprayed onto a water soluble, gel-forming solid particles. By these means, the core composed of water soluble gel-forming solid particles may absorb solvent residues and provide protection to probiotics placed onto said core.

SUMMARY OF THE INVENTION

According to at least some embodiments of the present invention, there is provided a formulation for a liquid product which undergoes heat treatment in at least one stage of its preparation or use, which preserves a sufficient amount of viable probiotic microorganisms, and methods for preparation and for use thereof.

The liquid food product for infants features viable bacteria in a sufficient amount even after adding to hot water or hot aqueous-based liquid before application. Thus, the food product for infants comprises a heat-stabilized probiotic composition, which exhibits a long shelf life.

The liquid food product comprises core granules containing probiotic bacteria, at least one substrate, and optionally other food grade ingredients, which are then coated with a starch based polymer. According to at least some embodiments, the starch based polymer comprises a component selected from the group consisting of native starch, thermoplastic starch, modified starch, starch derivatives, partially pre-gelatinized starch and pre-gelatinized starch; and/or one or more of carrageenan, guar gum and carob bean gum (also known as locust bean gum); or a combination thereof.

Optionally, the modified starch comprises one or more of Acid-treated starch (E1401), Alkaline-treated starch (E1402), Bleached starch (E1403), Oxidized starch (E1404), Starches, enzyme-treated (E1405), Monostarch phosphate (E1410), Distarch glycerol (E1411), Distarch phosphate esterified with sodium trimetaphosphate (E1412), Phosphated distarch phosphate (E1413), Acetylated distarch phosphate (E1414), Starch acetate esterified with acetic anhydride (E1420), Starch acetate esterified with vinyl acetate (E1421), Acetylated distarch adipate (E1422), Acetylated distarch glycerol (E1423), Hydroxypropyl starch (E1440), Hydroxypropyl distarch phosphate (E1442), Hydroxypropyl distarch glycerol (E1443), Starch sodium octenyl succinate (E1450).

According to at least some embodiments, the starch based polymer is selected from the group consisting of hydroxypropyl starch, phosphated distarch phosphate and acetylated distarch phosphate.

According to at least some embodiments, the cores are coated with two layers, an inner layer and an outer layer. Optionally and preferably, the outer layer becomes soluble at a higher temperature than the inner layer, more preferably upon contact with a liquid which may optionally comprise an aqueous solution, a dispersion, a suspension and so forth. For example and without limitation, the outer layer optionally starts to become soluble at 70° C., while the inner layer optionally starts to become soluble at 50° C. By "start to become soluble" it is meant that this temperature is the threshold at which the layer rapidly starts to dissolve or becoming soluble; clearly at temperatures above this threshold, the layer would dissolve much more rapidly. Preferably, there is a difference of at least 5° C., at least 10° C., at least 15° C., at least 20° C., at least 25° C., or at least 30° C. between the temperatures at which the inner and outer layers become soluble. Also optionally and preferably, the outer layer is also more viscous and forms a gel which is more stable and stronger than the inner layer at the same temperature. Thus the viscous gel of the outer layer takes longer to dissolve than the inner layer at the same temperature and especially at lower temperatures.

At each temperature at which a particular layer becomes soluble, dissolution preferably occurs after at least 30 seconds, 1 minute, 2 minutes, 3 minutes, 4 minutes or 5 minutes. Optionally and preferably, the rapidity of dissolution is different for each layer and is greater for the outer layer. Also optionally and preferably, dissolution of the inner layer starts only once dissolution of the outer layer is complete; by complete it is meant that the gel that is preferably initially formed by the outer layer upon contact with water or other liquid of at least the proper threshold temperature has also dispersed.

Optionally and more preferably, the inner layer comprises hydroxypropyl starch. Also optionally and more preferably, the outer layer comprises phosphated distarch phosphate, acetylated distarch phosphate or a combination thereof.

Optionally and most preferably, the liquid food product comprises core granules containing probiotic bacteria, at least one substrate, and optionally other food grade ingredients; an inner layer comprising hydroxypropyl starch; and an outer layer comprising phosphated distarch phosphate, acetylated distarch phosphate or a combination thereof.

According to some demonstrative embodiments, the existence of the inner and outer layers provides protection to the probiotic bacteria against exposure to heat and/or humidity. According to some embodiments of the present invention, additional protection layers may be added on top of the outer layer to provide additional protection to the liquid food product comprising the core granules of the present invention. For example, at least one water soluble polymer may be used as an additional protection layer to provide for a stabilized probiotic granule.

According to at least some embodiments, there is provided a process for the preparation of heat and humidity resisting probiotic bacteria in the form of stabilized probiotic granules, for a liquid-based healthy food product, comprising the steps of i) preparing core granules containing probiotic bacteria, at least one substrate, and optionally other food grade ingredients; ii) optionally coating said core granules by at least one inner layer, thereby obtaining sealed core granules; iii) coating said optionally sealed core granules by at least one outer layer comprising a thermo-sensitive, gel forming polymer; and iv) optionally coating said core granules comprising thermo-sensitive gel with an exterior coating layer comprising at least one water soluble polymer; thereby obtaining stabilized probiotic granules for admixing to a liquid-based food product, said probiotic granules comprising heat resistant and humidity resistant probiotic bacteria. The stabilized bacteria are capable to resist higher temperature even in the humid environment during manufacturing or preparing a liquid-based food product; an example of high temperature to be resisted is a pasteurization step when manufacturing a probiotic juice, or mixing an infant powder food comprising the granules of the invention with hot water when preparing baby food.

According to some demonstrative embodiments, the stabilized probiotic granules of the present invention may be capable of resisting high temperatures, for example, from room temperature (about 25° C.) and up to around 140° C.

In some demonstrative embodiments, the stabilized probiotic granules may be added to powdered infant formula, and exposed to a temperature that may be ranged between room temperature and 100° C.

According to other demonstrative embodiments, the stabilized probiotic granules may be added to any other liquid based infant product such as for example ready-to-use liquid infant formula which may undergo a pasteurization process, e.g., wherein the temperature range may be dependent on the pasteurization condition. For example a liquid infant formula may be heated at 280° F. (138° C.) for 8 sec and cooled to 73-80° F. (23-27° C.) in order to be pasteurized.

The invention relates to a process for the preparation of a liquid-based food product comprising a heating step, the product containing active probiotic bacteria, the process comprising i) preparing stabilized probiotic granules as described above; ii) admixing said stabilized probiotic granules into a semi-final product; iii) heating the mixture of said probiotic granules/particles and said liquid-based semi-final product at a predetermined temperature and for a predetermined time period; and iv) completing said liquid based semi-final product containing said stabilized probiotic granules by cooling down said mixture, thereby obtaining said liquid-based food product containing active probiotic bacteria. The term "semi-final product" describes a stage in the preparation of a food product according to the invention, in which said food product does not yet contain all the components or has not yet passed all the preparation steps, being not yet ready for the consumption. In a preferred embodiment of the invention, the process for the preparation of a liquid-based food product comprising a heating step, comprises i) preparing stabilized probiotic granules as described above; ii) admixing said stabilized probiotic granules/particles into a semi-final product comprising an infant powder food product, thereby obtaining a probiotic infant powder food product containing stabilized probiotic granules/particles; and iii) shortly before intended consumption of said probiotic infant powder food product, adding to said product cold water and heating or alternatively adding hot water, while keeping the mixture at a predetermined temperature for a predetermined time period. Said outer layer, composed of a thermo-sensitive gel forming polymer, forms a solid gel surrounding the probiotics core during said heating step, thereby preventing the transmission of the heat and humidity to the probiotics, while said gel dissolves after said cooling, allowing the pro-biotic material to be released in a desired liquid-based product.

The invention provides stabilized probiotic granules for admixing to a liquid-based food product, resistant to heating in an aqueous environment, comprising thermo-reversible gel-forming polymer. The stabilized probiotic granules of the invention comprise a core of probiotic bacteria in a substrate or mixed with a substrate, at least one inner layer coating said core, and at least one outer layer comprising a thermo-reversible gel forming polymer. The granules preferably comprise a core of probiotic bacteria with a substrate, at least one inner layer coating said core, and at least one outer layer comprising a thermo-reversible gel forming polymer, and at least one exterior layer comprising a water soluble polymer or erodible polymer. The granules of the invention preferably comprise a core of probiotic bacteria in a substrate, at least one outer layer comprising a thermo-reversible gel-forming polymer, and at least one exterior layer comprising a water soluble polymer or erodible polymer.

The substrate may comprise a component selected from the group consisting of supplement for bacteria, stabilizer, filler, binder, and a mixture thereof. Said substrate may comprises a prebiotic saccharide, wherein said inner layer may comprise a water soluble or erodible polymer, and wherein said outer layer may comprise a thermo-sensitive sol-gel forming polymer. In one embodiment, said substrate comprises a prebiotic saccharide, wherein said inner layer comprises a water soluble or erodible polymer, said outer layer comprises a thermo-sensitive sol-gel forming polymer, and wherein said exterior layer comprises a water soluble polymer or erodible polymer. Said substrate preferably comprises a prebiotic saccharide, wherein said outer layer comprises a thermo-sensitive sol-gel forming polymer, and wherein said exterior layer comprises a water soluble polymer or erodible polymer. The granules of the invention preferably have an outer layer composed of a thermo-sensitive gel-forming polymer which forms a solid gel surrounding the core granules when heated, thereby preventing the transmission of the heat and humidity to the probiotic bacteria, while said gel dissolves after cooling, allowing said bacteria to be released in a liquid-based product.

When using the term "liquid-based food product", intended is a product which has a high content of water, or which is intended for dispersing in water. Thus a liquid-based food product according to the invention may be a product having the form of liquid, suspension, emulsion, or paste, but it may be a powder intended for dispersing in water or water-based liquid, such as milk. In a preferred embodiment, said granules comprise a core of probiotic bacteria in a substrate, optionally at least one inner layer coating said core, at least one outer layer comprising a thermo-reversible gel-forming polymer, and optionally at least one outermost layer comprising a water soluble polymer. Said substrate may comprise a component selected from the group consisting of supplement for bacteria, stabilizer, buffering agent, chelating agent, filler, binder, and a mixture thereof. Said granules comprise, in one embodiment of the invention, a prebiotic saccharide in the core, a water soluble or erodible polymer in said inner layer, importantly a thermo-sensitive, sol-gel forming polymer in the outer layer, and a water soluble or erodible polymer in said outermost layer.

The invention provides a food product selected from infant food products, infant food powder compound, yogurt, dairy products, nectars, fruit juices, and energetic drinks/beverages, which product is a health food product comprising probiotic bacteria which were heat-stabilized as described above.

The term infant food products may refer for example to any soft, easily consumed food intended to be digested by a new-born, an infant, a baby and/or a toddler and may include breast-milk to be fortified, any infant formula, and any liquid and/or semi-solid food such as cereals, fruits, vegetables, meat and the like.

The invention, thus, relates to heat-processed or heat-processible healthy food beneficially affecting the consumer's intestinal microbial balance, wherein said heat-resistance and heat-processability are ensured by coating probiotic cores by layers which limit the transmission of heat and humidity to the probiotic bacteria and so increase their resistance during a heat step-comprising process.

BRIEF DESCRIPTION OF THE DRAWINGS

The above and other characteristics and advantages of the invention will be more readily apparent through the following examples, and with reference to the appended drawing, wherein:

FIG. 2. shows the structure of Pluronic, comprising an ABA tri-block copolymer comprising polypropylene oxide and polyethylene oxide.

FIG. 3. shows the sol-gel transition of Pluronic, an ABA triblock copolymer of polypropylene oxide and polyethylene oxide, as a function of temperature; the presence of polymer blocks having certain cloud point imparts the polymer with the property of being converted into a hydrophobic state at a temperature higher than the cloud point, and of being converted into a hydrophilic state at a temperature lower than the cloud point temperature; this results from the thermodynamic property of hydrophobic bonds increasing in strength with increasing temperature (and conversely decreasing in strength with decreasing temperature)

FIG. 4. shows the sol-gel transition of a cellulose derivative such as hydroxyl propyl cellulose (HPC) as a function of temperature; an increase over a critical temperature results in chain-chain interactions, including hydrophobic effects and hydrogen bonding, to dominate over chain-water hydrogen bonding; on the other hand, upon decreasing temperature below a critical temperature, water hydrogen bonding dominates over chain-chain interactions enabling the dissolution of the polymer.

DETAILED DESCRIPTION OF PREFERRED EMBODIMENTS

Figure 1:
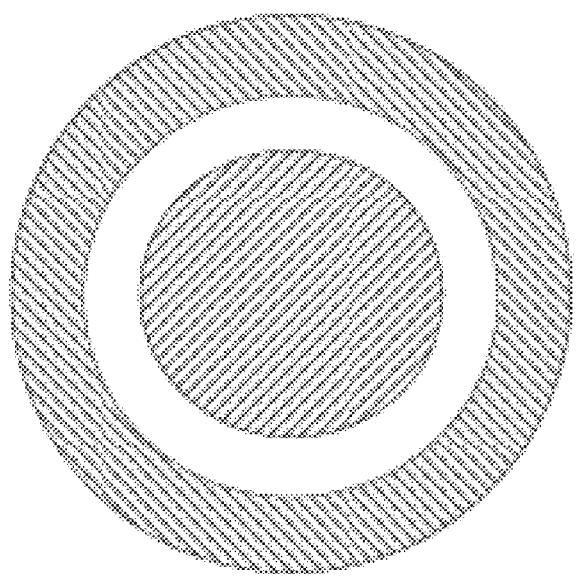
FIG. 1. shows a schema of a multiple-layered capsule according to one embodiment of the invention, to be comprised in healthy food; the encapsulation is designed to provide probiotic bacteria with maximum heat resistance during the heating step of either manufacturing process or preparation process; the core comprises probiotic bacteria and an absorbing substrate; the first layer adjacent to the core is the inner first sealing layer; the outer layer adjacent to said inner layer is the outer, thermo-reversible gel forming layer; alternatively, the core comprises probiotic bacteria and an absorbing substrate; the first layer adjacent to the core is the outer, thermo-reversible gel forming layer; the second layer adjacent to said outer layer is the exterior layer.

It has now been found that probiotic bacteria may be surprisingly efficiently stabilized for use in a heat-step comprising process by coating with a sol-gel forming polymer. The bacteria were formulated in a granulated core coated with one or more coating layer, thereby obtaining probiotic compositions providing viable probiotic organisms even after heating at relatively high temperatures at high humidity, the composition being further stable on storage and capable of administering viable bacteria to the gastro-intestinal tracts after the oral administration. The invention provides granular probiotics to be used as healthy food additives. The present invention is particularly directed to a process for the preparation of liquid-based food, such as infant food powder compound which is substantially suspended in hot water (about 70° C.), fruit juices, nectars, yogurts, milk-based dairy products and energetic drinks containing heat resisting probiotics.

According to some embodiments, infant formulas may come in three basic forms: ready-to-use, liquid concentrate, and powdered. The ready-to-feed (or ready-to-use) infant formula is a liquid infant formula which may be a formula that may be consumed without requiring additional compositional changes such as the addition of water prior to consumption, or a reconstituted powdered infant formula made by mixing water (sterile water) with powdered formulas such as those available commercially from Mead Johnson & Company (Enfamil® Infant Formula) or Ross Laboratories (Similac® Infant Formula). Ready-to-use liquid infant formula may be the most convenient—no mixing or measuring required, just open and serve. It's the kind of formula that hospitals often give to newborns. It's hygienic and especially helpful when one does not know whether he will have access to safe water. Ready-to-use liquid infant formula is a pasteurized product and once opened, the formula has a short lifespan—it must be used within a few hours (ready-to-feed infant formula can be refrigerated for up to 72 hours after opening and then needs to be discarded).

In contrast to the powdered infant formula, the ready-to-use liquid infant formula needs to be pasteurized before filling into bottles. The commercial ready-to-use liquid infant formula compositions are produced using pasteurization. Pasteurization requires that the milk be heated to specific temperatures for specific times. The pasteurization process kills all pathogens and most of the microorganisms responsible for spoilage. Commercial ready-to-use formula compositions containing probiotics can be produced by adding the probiotic to the formula prior to pasteurization, but the pasteurization process will kill many of the probiotic microorganisms and thus prevent the infant from getting a sufficient dose of probiotics when the formula is consumed. Similarly, ready-to-use formula compositions containing probiotics can be produced by adding the probiotic to the formula after pasteurization just before filling the formula into its container. The problem arising from the latter is the possibility of inserting a contaminant into already pasteurized liquid formula. This subsequently may cause contamination of the formula by harmful bacteria and also shortens the shelf-life.

Methods for increasing the shelf-life and improving viability have included searching for improved strains and adding various compounds such as preservatives (such as ascorbic acid) and growth factors to the formula. As a result of these limitations, the current commercial ready-to-use liquid infant formula containing probiotics may not have the number of probiotic microorganisms needed to confer the desirable health benefits. Also, such formula compositions readily spoil within a relatively short time and what is not sold and consumed has to be discarded as waste.

Using the technology according to the present invention one can provide an extended shelf-life for ready-to-use infant formula, containing probiotics that remain viable both during the production process and throughout shelf-life. Furthermore, the product which will be prepared using the technology described herein will be purified of any contaminant and still contain the recommended dose of viable probiotics beneficial to health.

According to some embodiments, and based on the production process of most manufacturers, the manufacturing process of ready-to-use liquid formula is as follows:

1. Preparation of Bulk, Ready-to-Use Infant Formula

Figure 8:
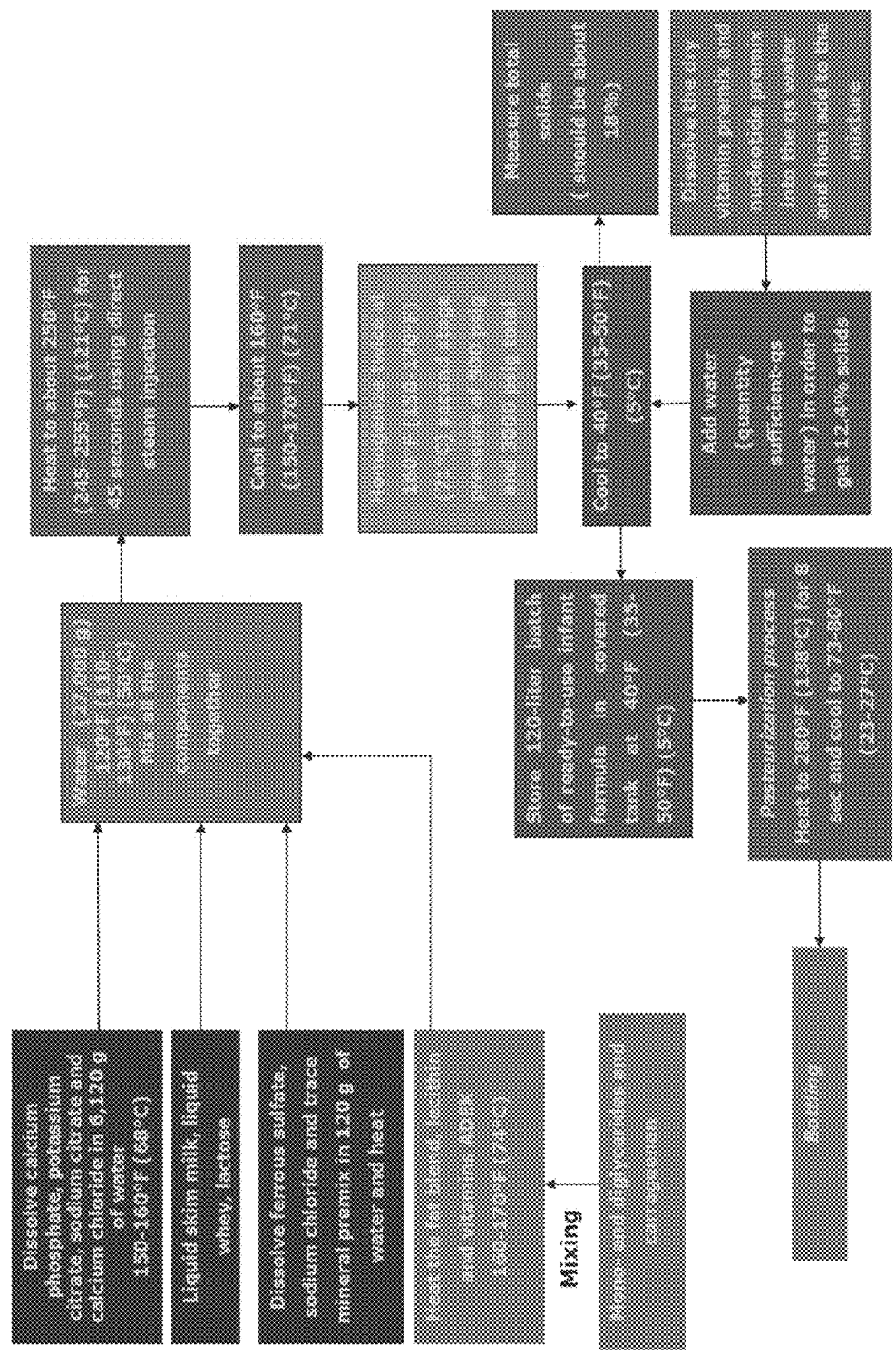
FIG. 8. Is a flow chart diagram of the manufacturing process of ready-to-use liquid infant formula, according to some demonstrative embodiments described herein.

During this process all components of the ready-to-use infant liquid formula are either dissolved or dispersed and homogenized in water. The flow chart of the process is demonstrated in FIG. 8. The result is a 120-liter batch of ready-to-use infant formula containing the ingredients summarized in the Table 1 as follows:

TABLE 1

| Ingredients and their quantities composing the ready-to-use liquid infant formula ||
| --- | --- |
| Ingredient | Amount (grams) |
| Liquid whey | 6412.04 grams |
| Fat blend | 4193.1 |
| Liquid skim milk | 2294.81 |
| Lactose | 2273.39 |
| Potassium citrate | 93.56 |
| Mono- and diglycerides | 86.80 |
| Calcium phosphate | 50.22 |
| Dry Vitamin Premix | 45.19 |
| Lecithin concentrate | 44.33 |
| Carrageenan | 33.91 |
| Calcium chloride | 31.80 |
| Sodium chloride | 16.92 |
| Nucleotide premix | 8.35 |
| Ascorbic acid | 8.11 |
| Ferrous sulfate | 7.30 |
| Sodium citrate | 5.46 |
| Vitamin A, D, E, $K_1$ Concentrate | 3.89 |
| Trace mineral premix | 3.65 |
| Water, quantity sufficient to | 120 liters |

According to some embodiments, the final preparation may be stored in a covered tank for the following stage which is a pasteurization and bottling process.

Figure 9:
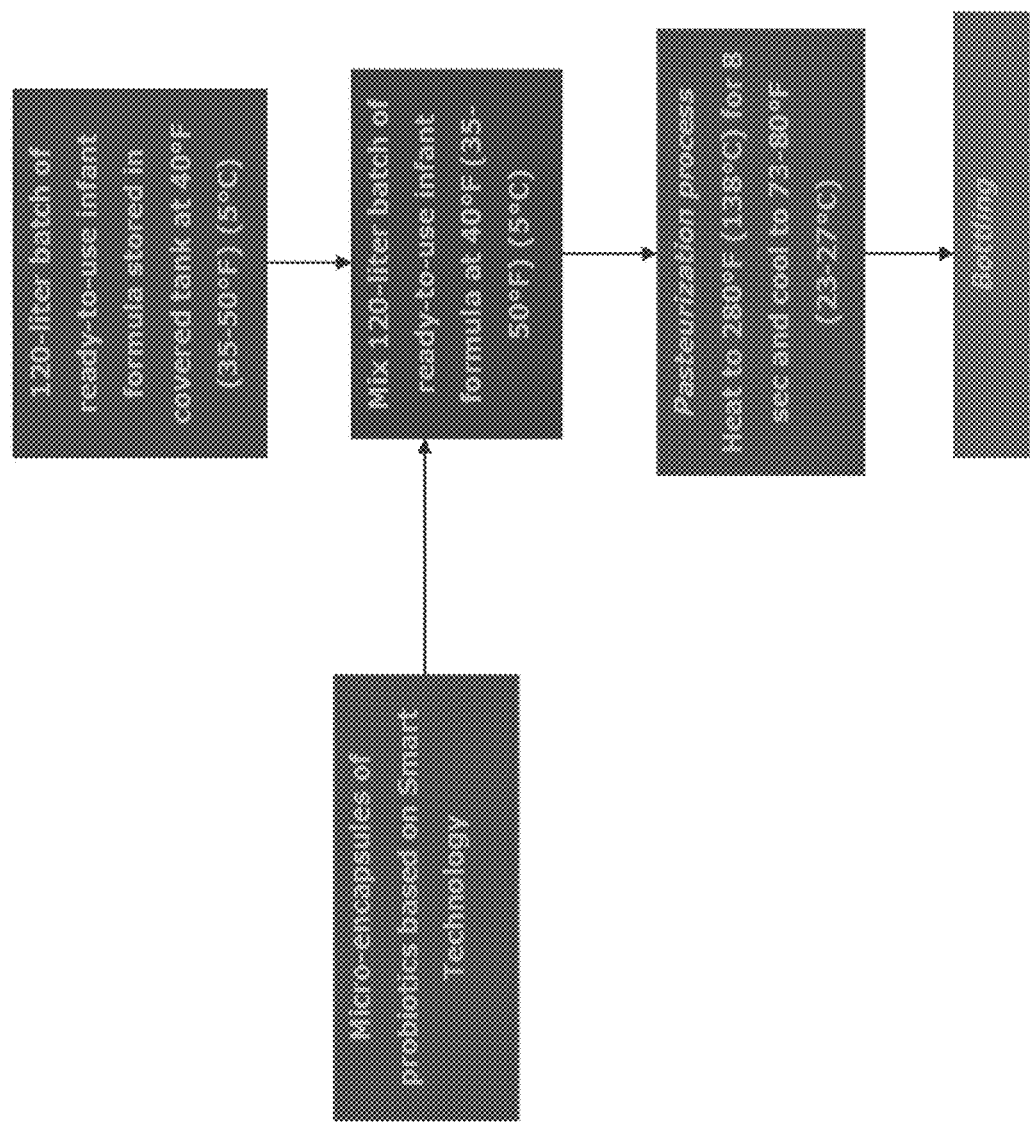
FIG. 9. Is a flow chart diagram of the stage at which the microencapsules of probiotics of the present invention can be added into the ready-to-use liquid infant formula, according to some demonstrative embodiments described herein.

The microencapsulated probiotic bacteria of the present invention can be added to a container of the batch of ready-to-use infant formula prepared as described above at this stage just before pasteurization process as demonstrated in FIG. 9.

2. Pasteurization Process

The infant formula may be heated at 280° F. (138° C.) for 8 sec and cooled to 73-80° F. (23-27° C.). The infant formula is bottled into sterilized 3-oz glass bottles and capped with sterilized closures. Alternatively, the liquid infant formula can be bottled first, prior to pasteurization, and then pasteurized followed by capping.

During the pasteurization process utilizing the technology of the present invention provides the bacteria with superior protection and stability, resulting in a high viability of bacteria. The bacteria are totally released after the temperature is cooled down upon full dissolution of the microencapsuled layers. By these means the resulting liquid infant formula will be totally pasteurized and still have a high level of viable probiotics. According to some demonstrative embodiments, the stabilized granules of the present invention may be added to any infant formula, whether in a liquid concentrate state, powdered state or ready-to-use state.

The composition of the present invention, comprising the stabilized granules, can be added essentially at any stage prior to or post pasteurization of the infant formula.

According to some demonstrative embodiments, adding the composition of the present invention to the infant formula before pasteurization occurs will enable the eradication of harmful pathogens that may exist in the formula, yet refrain from harming the probiotic bacteria contained within the stabilized granules of the composition of the present invention.

In the case of powdered formula, the composition of the present invention may be added at essentially any stage of production of the formula, whereas upon final preparation of the formula, i.e., right before feeding, hot water (at least 60° C., and preferably 70° C. and above) is added to the powdered formula. The addition of the hot water right before use may enable the eradication of harmful pathogens that may exist in the formula, yet it will essentially not harm the probiotic bacteria contained within the stabilized granules of the composition of the present invention.

The invention provides a process for the preparation of liquid-based food, comprising the steps of i) preparing a core (granules) that comprises probiotic bacteria; ii) optionally coating said core (granules) by at least one inner layer comprising a water soluble polymer for preventing humidity penetration into the core (granules); iii) coating said granules by at least one outer layer comprising a thermo-reversible gel-forming (sol-gel) polymer for resisting heat and humidity, thereby obtaining a stabilized probiotic granule; iv) optionally coating said core (granules) by at least one outermost layer comprising a water soluble polymer; v) admixing said stabilized probiotic granules to a liquid-based food pre-product (semi-final product); and vi) completing the preparation the said liquid-based food pre-product containing said stabilized probiotic granules by heat treatment at predetermined temperature for predetermined time. In an important embodiment of the invention, said stabilized probiotic granules are added to a solid-based food product such as powder product (like infant food powder compound), which should be eventually added to hot water (up to 70° C.) before using, and allowed to cool down before consumption. In an important embodiment of the invention, said stabilized probiotic granule has a core comprising probiotic bacteria and a substrate, to which said bacteria are absorbed or with which they are granulated, said core containing additionally other nutritionally acceptable excipients; the granule has optionally further an inner layer of water soluble polymer; the granule has an outer layer of thermo-sensitive (thermo-reversible) gel forming polymer having a sol-gel transition (transition temperature); the granule has optionally an exterior layer of water soluble polymer. In another important embodiment of the invention, both said inner layer and said outer layer comprise thermo-sensitive gel forming polymers having a sol-gel transition, but with different molecular weights or viscosities. In another important embodiment of the invention, both said inner layer and said exterior layer comprise similar polymers having similar molecular weights or viscosities or similar polymers but with different molecular weights or viscosities. In another important embodiment of the invention, said stabilized probiotic granule has a core comprising probiotic bacteria and a substrate in which said bacteria are granulated or absorbed, said granule containing additional excipients, and further a single layer of thermo-sensitive gel forming polymer having a sol-gel transition. In another important embodiment of the invention, said stabilized probiotic granule has a core comprising probiotic bacteria and a substrate in which said bacteria are absorbed or granulated and said granule containing additionally other acceptable excipients; an outer layer of thermo-sensitive gel forming polymer having a sol-gel transition; an exterior layer of water soluble polymer. In another embodiment of the invention, said stabilized probiotic granule has a core comprising probiotic bacteria and a substrate in which said bacteria are absorbed or granulated and said granule containing additionally other acceptable excipients; an inner layer of water soluble polymer; and two outer layers including a lower, enteric layer providing gastric resistance, and an upper layer of thermo-sensitive gel forming polymer having a sol-gel transition.

According to some demonstrative embodiments, both said inner layer and said outer layer may comprise thermo-sensitive gel forming polymers having a sol-gel transition, but with different molecular weights or viscosities. According to these embodiments, selecting thermo-sensitive gel forming polymers with different molecular weights and/or viscosities enables the production of probiotic granules which may be resistant to different temperatures and/or humidity levels.

In a preferred embodiment, the preferred process of the invention comprises granulating probiotic bacteria, coating them by at least one inner layer for resisting humidity, at least one outer layer for resisting production (manufacturing) heat and/or humidity, wherein said resisting occurs at a predetermined production temperature for predetermined heat process time, after which said second layer is swelled forming gel during exposing to high temperature, so preventing the penetration of the hot liquid into the core containing said probiotics, allowing the probiotic bacteria to be safe from heating, and then to be released into a liquid food product, when the outer layer or exterior layer dissolves on cooling. A process according to the invention includes, in a preferred embodiment, preparing a stabilized probiotic granule having i) a core with probiotic bacteria which may contain at least one stabilizing agent, antioxidant, sugar, filler, binder, and other excipients, and further having ii) an inner layer coating the core comprising a water soluble polymer preventing the permeation of water and humidity into the core, and further having also iii) an outer layer coating said core and said inner layer, where said outer layer comprises at least one thermo-reversible gel forming polymer having a sol-gel transition temperature. In another preferred embodiment, the preferred process of the invention comprises granulating probiotic bacteria, coating them by at least one outer layer (first layer) for resisting production (manufacturing) heat and humidity, wherein said resisting occurs at a predetermined production temperature for predetermined heat process time, after which said outer layer is swelled forming gel during exposing to high temperature, so preventing the penetration of the hot liquid into the core containing said probiotics, allowing the probiotic bacteria to be safe from heating, and then to be released into said liquid food product, when the outer layer dissolves on cooling; and at least one outermost layer (second layer) for enhancing the dissolution of said outer layer (first layer) on cooling. In another preferred embodiment, the preferred process of the invention comprises granulating probiotic bacteria, coating them by at least one inner layer for resisting humidity (first layer); at least one outer layer (second layer) for resisting production (manufacturing) heat and humidity, wherein said resisting occurs at a predetermined production temperature for predetermined heat process time, after which said outer layer is swelled forming gel during exposing to high temperature, so preventing the penetration of the hot liquid into the core containing said probiotics, allowing the probiotic bacteria to be safe from heating, and then to be released into said liquid food product, when the outer layer dissolves on cooling; and at least one exterior layer (third layer) for enhancing the dissolution of said outer layer (second layer) on cooling.

A process according to the invention includes, in a preferred embodiment, preparing a stabilized probiotic granule having i) a core with probiotic bacteria and which may contain at least one stabilizing agent, antioxidant, sugar, filler, binder, and other excipients and further having ii) an inner layer coating the core comprising of a water soluble polymer preventing the permeation of water and humidity into the core, and further having also iii) an outer layer coating said core and said inner layer, where said outer layer comprises at least one thermo-reversible gel forming polymer having a sol-gel transition temperature, wherein said inner layer comprises at least one thermo-reversible gel forming polymer having a sol-gel transition temperature which can chemically be either similar to or different from said outer layer.

The invention provides a stabilized probiotic granule comprising i) a core comprising probiotic bacteria and a substrate on which said bacteria are absorbed or coated; ii)

optionally an inner layer comprising a polymer preventing the permeation of water and humidity into the core coating said core; iii) at least one outer layer, coating said core and said inner layer, comprising thermo-sensitive polymer having a sol-gel transition temperature; and iv) optionally an exterior layer comprising a polymer enhancing the dissolution of said outer layer (first layer) on cooling. Said core preferably further comprises one or more supplemental agents for said bacteria, for example prebiotic oligosaccharides.

In a preferred embodiment of the invention, said probiotic bacteria comprise a genus selected from *Lactobacillus* and *Bifidobacterium*. The stabilized probiotic core granule or core mixing according to the invention is a coated granule, comprising at least two layered phases, for example a core and two coats, or a core and three or more coats. Usually, one of the coats contributes mainly to prevention of water or humidity penetration into the core during the coating of the outer layer or during later stages, such as when the ultimate multilayered probiotics are suspended in a liquid-based product during the preparation of said liquid-based product or during the coating processes. Another outer coat contributes to the heat resistance during the liquid-based food product processing. Another exterior coat contributes to the enhancing dissolution of said outer thermo-sensitive gel forming layer on cooling. Usually, it is one of the layers that contributes maximally to said heat resistance and water or humidity penetration into the core; however, the stabilized probiotic granule of the invention may comprise more layers that contribute to the process stability of the bacteria, as well as to their stability during storing said food and during safe delivery of the bacteria to the intestines. Likewise, the two inner and exterior coats may be the same polymers with either same or different viscosities or molecular weights. Likewise, one thermo-sensitive gel-forming polymer may be used for coating the core particles, whereby one single coating layer provides protection against water and humidity penetration into the core, as well as resistance against heat and humidity.

The invention is directed to a process of manufacturing healthy food, comprising i) mixing a suspension of probiotic bacteria with a substrate and with supplemental agents for the bacteria, thereby obtaining a core mixture; ii) coating particles of said core mixture with an inner water soluble polymer; iii) coating said coated particles with an outer polymer layer, which said outer polymer layer confers stability to said bacteria under the conditions of heat and humidity, thereby obtaining particles coated with two layers. The invention is also directed to a process of manufacturing healthy food, comprising i) mixing a suspension of probiotic bacteria with a substrate and with supplemental agents for the bacteria, thereby obtaining a core mixture; ii) optionally coating particles of said core mixture with an inner water soluble polymer; iii) coating said coated particles with an outer polymer layer; optionally coating said coated particles of said core mixture with an exterior water soluble polymer, which said outer polymer layer confers stability to said bacteria under the conditions of heat and humidity, thereby obtaining particles coated with three layers. The invention is also directed to a process of manufacturing healthy food, comprising i) granulation of probiotic bacteria with substrates and with supplemental agents for the bacteria, thereby obtaining core granule particles; ii) coating particles of said core granule with an inner water soluble polymer; iii) coating said coated particles with an outer polymer layer, which said outer polymer layer confers stability to said bacteria under the conditions of heat and humidity, thereby obtaining particles coated with two layers. The invention is also directed to a process of manufacturing healthy food, comprising i) granulation of probiotic bacteria with substrates and with supplemental agents for the bacteria, thereby obtaining core granule particles; ii) coating particles of said core granule with an outer polymer layer, which said outer polymer layer confers stability to said bacteria under the conditions of heat and humidity; iii) coating said coated particles with an exterior water soluble polymer, thereby obtaining particles coated with two layers. The invention is also directed to a process of manufacturing healthy food, comprising i) granulation of probiotic bacteria with substrates and with supplemental agents for the bacteria, thereby obtaining core granule particles; ii) coating particles of said core granule with an inner water soluble polymer; iii) coating said coated particles with an outer polymer layer, which said outer polymer layer confers stability to said bacteria under the conditions of heat and humidity; iv) coating said coated particles with an exterior water soluble polymer, thereby obtaining particles coated with three layers.

In a preferred process of manufacturing probiotic food, an aqueous suspension of probiotic bacteria is mixed with at least one substrate and at least one oligosaccharide, and optionally other food grade additives such as stabilizers, fillers, binders, antioxidant, and etc., thereby obtaining a wet core mixture; particles of said wet core mixture are dried, thereby obtaining a core mixture; particles of said core mixture are coated with an inner coating layer polymer preventing or reducing the penetration of water or humidity into said core, thereby obtaining water sealed coated particles; said water sealed coated particles are coated with a thermo-reversible gel-forming polymer. Said at least one substrate may comprise galactan, galactose or a mixture thereof, said at least one oligosaccharide may comprise, galactan, maltodextrin, and trehalose, said other food grade additives comprise stabilizer, antioxidant, filler and binder, said inner coating layer polymer may comprise hydroxypropyl methyl cellulose, and/or polyvinyl-based polymer, and said thermo-reversible gel forming polymer may comprise hydroxypropyl cellulose and/or copolymer of polypropylene glycol and polyethylene glycol (Pluronic). In another preferred process of manufacturing probiotic food, an aqueous suspension of probiotic bacteria is mixed with at least one substrate and at least one oligosaccharide, and optionally other food grade additives such as stabilizers, fillers, binders, antioxidant, and etc., thereby obtaining a wet core mixture; particles of said wet core mixture are dried, thereby obtaining a core mixture; particles of said core mixture are coated with an outer coating layer comprising thermo-reversible gel forming polymer, thereby obtaining a thermo-sensitive polymer coated core mixture; particles of said thermo-sensitive polymer coated core mixture are coated with an exterior water soluble polymer enhancing the dissolution of said thermo-reversible gel forming polymer on cooling. Said at least one substrate may comprise galactan, galactose or a mixture thereof, said at least one oligosaccharide may comprise, galactan, maltodextrin, and trehalose, said other food grade additives comprise stabilizer, antioxidant, filler and binder, said thermo-reversible gel forming polymer may comprise hydroxypropyl cellulose and/or copolymer of polypropylene glycol and polyethylene glycol (Pluronic); and said outermost coating layer polymer may comprise hydroxypropyl methyl cellulose, and/or polyvinyl-based polymer.

Another preferred process of manufacturing micro encapsulated probiotic bacteria according to the invention includes the following steps:
1. Drying mix of probiotics mixture, with at least one substrate and at least one oligosaccharide, and optionally other food grade additives such as stabilizers, fillers, binders, antioxidant, and etc., thereby obtaining a core mixture.
2. Granulating said core mixture using a binder solution in purified water, thereby obtaining a core granule.
3. Optionally coating particles of said core granule with an inner coating layer polymer preventing or reducing the penetration of water or humidity into said core, thereby obtaining water sealed coated particles.
4. Coating said water-sealed coated particles with a thermo-reversible gel-forming polymer.
5. Optionally coating particles of said core granule with an exterior coating layer polymer enhancing the dissolution of said thermo-reversible gel forming polymer on cooling below its cloud point or its lower critical solution temperature (LCST).

The invention provides probiotic compositions comprising the stabilized probiotic granules described above, which granules exhibit high heat resistance and long storage stability. The composition according to the invention is preferably a healthy food product, for example food product selected from the group consisting of infant food products, infant food powder compounds, yogurts, dairy products, nectars, and fruit juices. Said food product was exposed to higher than ambient temperature during either production process or preparation process.

In one aspect, the present invention is directed to a process for the preparation of liquid-based food products containing probiotics, such as probiotic fruit juices, nectars, yogurts, milk-based dairy products, energetic drinks/beverages, and infant food powder compound to be suspended in hot water (about 70° C.). A mixture that comprises probiotic material is prepared and then converted to granules, e.g., by fluidized bed technology such as Glatt or turbo jet, Glatt or an Innojet coater/granulator, or a Huttlin coater/granulator, or a Granulex. The resulting granules, are encapsulated by a first layer, preferably a water soluble polymer layer for resisting water or humidity penetration into the core granule which may occur in the further steps of heat resistance probiotic composition preparation then by a second layer with a thermo-sensitive gel forming polymer for resisting heat at a predetermined temperature for a predetermined time period. Alternatively, the resulting granules, are encapsulated by an outer layer (first layer) with a thermo-sensitive gel forming polymer for resisting heat at a predetermined temperature for a predetermined time period then by a second layer (exterior layer) preferably a water soluble polymer layer for enhancing the dissolution of said thermo-sensitive gel forming polymer on cooling below its cloud point or its lower critical solution temperature (LCST). Alternatively, the resulting granules, are encapsulated by a first layer (inner layer), preferably a water soluble polymer layer for resisting water or humidity penetration into the core granule which may occur in the further steps of heat resistance probiotic composition preparation then by a second layer (outer layer) with a thermo-sensitive gel-forming polymer for resisting heat at a predetermined temperature for a predetermined time period then by a third layer (exterior layer) preferably a water soluble polymer layer for enhancing the dissolution of said thermo-sensitive gel forming polymer on cooling below its cloud point or its lower critical solution temperature (LCST). Then resulting micro-encapsulated probiotics according to the above steps is introduced to a liquid-based product which must undergo a heating step during its preparation process. Alternatively the above resulting microencapsulated probiotics can be added to a food product being a solid powder mixture, such as an infant food powder, which should further be added to a hot water (usually up to 70° C.). During the exposure of the above resulted microencapsulated probiotics to heat, during the preparation process of liquid-based food product, the outer layer, which is composed of a thermo-sensitive gel forming polymer, forms a solid gel surrounding the probiotics core granule preventing the transmission of the heat and humidity to the probiotics. After lowering the temperature, the outer thermo-sensitive gel forming layer dissolves, allowing the pro-biotic material to be released in the liquid-based product. The double or triple encapsulated granules can advantageously be added to a solid powder mixture food product such as an infant food powder compound. In this case before consuming the solid powder, it should be added to a hot water which has up to 80° C. preferably 70° C., to prepare an appropriate suspension. Again, during the exposure of the microencapsulated probiotics, according to the present invention, to the hot water, as described above, the most outer layer which is composed of a thermo-sensitive gel forming polymer forms a solid gel surrounding the probiotics core, preventing the transmission of the heat to the probiotics. After letting the suspension cool down, the outer thermo-sensitive gel forming layer is dissolved to allow the pro-biotic material to be released in the infant suspension. The invention thus provides a liquid-based food product containing probiotics which survive the heating step needed during the preparation of the product for human uses, such as, yogurt, dairy products, nectars, and fruit juice. The product consists of: a) encapsulated granules, made of a mixture that comprises probiotic material which is dried and converted to core granules to be encapsulated by optionally an inner layer (first layer), preferably a water soluble polymer layer for resisting water and humidity penetration into the core granules, and by an outer layer (second layer) comprises at least one thermo-sensitive gel forming polymer resisting transition heat and humidity in the core granules for a predetermined manufacturing temperature and time, after which the second layer is being dissolved upon cooling down to allow the pro-biotic material to be released in the liquid-based food product, and optionally by an exterior layer (third layer layer), preferably a water soluble polymer layer for enhancing the dissolution of said thermo-sensitive gel forming polymer on cooling below its cloud point or its lower critical solution temperature (LCST); and b) an infant food product or an infant food powder compound to which the micro-encapsulated granules according to the present invention are previously added. Before consumption, the mixture of infant food product or infant food powder compound and the micro-encapsulated granules according to the present invention is added into a hot water (preferably about 70° C.).

So, provided is a process for preparing probiotic bacteria capable of being heated during manufacturing or preparing food with high rates of survivability. According to one embodiment of the present invention, the first step in making said probiotic food is preparing a core or granules comprising dried probiotic bacteria, These granules are then encapsulated by optionally a first water soluble polymer layer. The first layer helps to resist the water and humidity penetration into the granules. The second layer is then created comprising at least one thermo-sensitive gel forming polymer. Optionally a third layer is then created comprising at least one a water soluble polymer layer for enhancing the dissolution of said thermo-sensitive gel-forming polymer on cooling below its cloud point or its lower critical solution temperature (LCST). The encapsulated granules are then added to a liquid based food product right before the final preparation. The second layer is dissolved after cooling the liquid-based food product at the end of the preparation process, allowing the probiotic material to be released from the encapsulated granules into the liquid-based product.

The Inner Coating Layer:

According to further features of the preferred embodiments of the invention, the encapsulated probiotics further comprise an inner coating, which is layered between the inner core and the thermo-reversible outer sol-gel coating layer. Example of materials that may be used for the first coating layer may be selected from the group consisting of water soluble or erodible polymers such as, for example, Povidone (PVP: polyvinyl pyrrolidone), Copovidone (copolymer of vinyl pyrrolidone and vinyl acetate), polyvinyl alcohol, Kollicoat Protect (BASF) which is a mixture of Kollicoat IR (a polyvinyl alcohol (PVA)-polyethylene glycol (PEG) graft copolymer) and polyvinyl alcohol (PVA), Opadry AMB (Colorcon) which is a mixture based on PVA, Aquarius MG which is a cellulose-based polymer containing natural wax, lecithin, xanthan gum and talc, low molecular weight HPC (hydroxypropyl cellulose), low molecular weight HPMC (hydroxypropyl methylcellulose) such as hydroxypropylcellulose (HPMC E3 or E5) (Colorcon), methyl cellulose (MC), low molecular weight carboxy methyl cellulose (CMC), low molecular weight carboxy methyl ethyl cellulose (CMEC), low molecular weight hydroxyethylcellulose (HEC), low molecular weight hydroxyl ethyl methyl cellulose (HEMC), low molecular weight hydroxymethylcellulose (HMC), low molecular weight hydroxymethyl hydroxyethylcellulose (HMHEC), low viscosity of ethyl cellulose, low molecular weight methyl ethyl cellulose (MEC), gelatin, hydrolyzed gelatin, polyethylene oxide, water soluble gums, water soluble polysaccharides, acacia, dextrin, starch, modified cellulose, water soluble polyacrylates, polyacrylic acid, polyhydroxyethylmethacrylate (PHEMA), polymethacrylates, their copolymers, and/or mixtures thereof.

More preferably the inner first coating layer polymers are low molecular weight HPMC (hydroxypropyl methylcellulose) such as hydroxypropylcellulose (HPMC E3 or E5) (Colorcon), polyvinyl alcohol, Kollicoat Protect (BASF) which is a mixture of Kollicoat IR (a polyvinyl alcohol (PVA)-polyethylene glycol (PEG) graft copolymer) and polyvinyl alcohol (PVA) and silicon dioxide, Opadry AMB (Colorcon) which is a mixture based on PVA, and Aquarius MG which is a cellulose-based polymer containing natural wax. Theses polymers provide superior barrier properties against water/humidity penetration into the core. Optionally the inner first coating layer may further comprise an excipient which may be at least one of a glidant, a surfactant, filler, a solubilizer, and a buffering agent.

Outer Heat Resisting Coating Layer:

The outer coating layer provides heat resistance and also prevents the water and humidity penetration into the core. This coating layer comprises a thermo-reversible (thermosensitive) sol-gel forming polymer. Thermo-reversible sol-gel forming polymer or thermo-sensitive sol-gel forming polymer belongs to a category of physical transitions which do not require use of organic solvents, chemical cross-linking reactions or externally operated devices (e.g. photopolymerization) in order to form gel upon contact with aqueous solution at a predetermined situation, and thus are less likely to induce toxicities to the surrounding media.

Temperature sensitive polymers show abrupt changes in their solubility as a function of environmental temperature. This property was employed to develop aqueous solutions of these polymers which undergo sol-gel transition in response to temperature changes. At lower critical solution temperature (LCST), the interaction forces (hydrogen bonding) between water molecules and polymer become unfavorable compared to polymer-polymer and water-water interaction and phase separation occurs as the polymer dehydrates. Consequently, aqueous polymer solutions display low viscosity at ambient temperature but exhibit a sharp increase in viscosity following temperature rise, forming a semi-solid gel. One major advantage of formulations based on such polymers is their ability to form a stable gel which does not dissolve at higher temperature and which swells in aqueous media preventing water penetration inside to the core. The swelled stable gel further prevents the effect of the high temperature on the inner core. A number of polymers exhibit abrupt changes in their aqueous solubility with an increased temperature; the resulting sol-gel transition occurring at the lower critical solubility temperature (LCST) is characterized by minimal heat production and absence of byproducts. According to some embodiments, the absence of byproducts is especially important in the case of newborns, small infants and children in general, which are more liable to be affected by the presence of unwanted or harmful byproducts. The "cloud point" represents the temperature at which a water-soluble compound begins to come out of solution with resulting scattering of light or "cloud" formation. The polymer-polymer and the polymer-solvent interactions (solvent that in food applications will be usually water) show an abrupt re-adjustment in small ranges of temperature, and this is translated to a chain transition between extended and compacted coil states. Temperature-responding polymers present a fine hydrophobic-hydrophilic balance in their structure, and small temperature changes around the critical solubility temperature (LCST) make the chains collapse or expand, while responding to the new adjustments of the hydrophobic and hydrophilic interactions between the polymeric chains and the aqueous media.

Considering the free energy of association (ΔG) between the polymer chains:

$$\Delta G = \Delta H - T \Delta S$$

where ΔH is the enthalpy term, ΔS the entropy term and T temperature, it can be concluded that increase over a critical temperature results in a larger value of TΔS than the positive enthalpy term (ΔH), and thus a negative ΔG favoring polymer association: chain-chain interactions (hydrophobic effects, hydrogen bonding) dominate over chain-water hydrogen bonding. On the other hand upon decreasing temperature below a critical temperature, water hydrogen bonding dominates over chain-chain interactions thus the dissolution of the polymer may occur. Macroscopic response of the polymer will depend on the physical state of the chains. If the macromolecular chains are linear and solubilized, the solution will change from mono-phasic to biphasic due to polymer precipitation when the transition occurs. Polymer solution is a free-flowing liquid at ambient temperature and gels at high temperature. In some cases, if lowering the amount of thermo-gelling polymer is necessary, it may be blended with a pH-sensitive reversibly gelling polymer.

Block copolymers containing one block with a LCST at a temperature range where the other block is soluble, self assemble in response to temperature increase. Morphology of the self-assembled structure depends on copolymer architecture and MW; micelles or networks of infinite MW (gels) can be obtained by appropriate design. A recently reported, alternative approach was based on interpenetrating networks of poly(N-isopropylacrylamide) (PNIPAM) and poly(acrylic acid) (PAAc), formulated in nanoparticles. The collapse of PNIPAM above its LCST triggered the bonding of the NPs into a network while the repulsion between the charged PAAc chains prevented agglomeration.

The thermo-sensitive polymers exhibiting thermally-driven phase transitions may be selected from the group consisting of poly-N-substituted acrylamide derivatives such as poly(N-isopropylacrylamide) (PNIPAM), Poly-N-acryloylpiperidine, Poly-N-propylmethacrylamide, Poly-N-isopropylacrylamide Poly-N-diethylacrylamide, Poly-N-isopropylmethacrylamide, Poly-N-cyclopropylacrylamide, Poly-N-acryloylpyrrolidine, Poly-N,N-ethylmethylacrylamide, Poly-N-cyclopropylmethacrylamide, Poly-N-ethylacrylamide, poly-N-substituted methacrylamide derivatives, copolymers comprising an N-substituted acrylamide derivative and an N-substituted methacrylamide derivative, copolymer of N-isopropylacrylamide and acrylic acid, polypropyleneoxide, polyvinylmethylether, partially-acetylated product of polyvinyl alcohol, copolymers comprising propyleneoxide and another alkylene oxide such as non-ionic, amphiphilic poly(ethylene glycol)-bl-poly(propylene glycol)-bl-poly(ethylene glycol) (PEGPPG-PEG) block copolymer (also referred to as Tetronics®, poloxamer, Pluronic®), Poloxamer-co-PAAc, Oligo(poloxamers), Methylcellulose (MC), hydroxylpropylcellulose (HPC), methylhydroxyethylcelluloce (MHEC), hydroxylpropylmethylcellulose (HPMC), hydroxypropylethylcellulose (HPEC), hydroxymethylpropylcellulose (HMPC), ethylhydroxyethylcellulose (EHEC) (Ethulose), hydroxyethylmethylcellulose (HEMC), hydroxymethylethylcellulose (HMEC), propylhydroxyethylcellulose (PHEC), hydrophobically modified hydroxyethylcellulose (NEXTON), amylose, amylopectin, Poly(organophosphazenes), natural polymers like xyloglucan, or a mixture thereof.

The above mentioned poly-N-substituted acrylamide derivatives may be either a homopolymer or a copolymer comprising a monomer constituting the above polymer and "another monomer". The "another monomer" to be used for such a purpose may be a hydrophilic monomer, or a hydrophobic monomer. In general, when copolymerization with a hydrophilic monomer is conducted, the resultant cloud point temperature may be increased. On the other hand, when copolymerization with a hydrophobic monomer is conducted, the resultant cloud point temperature may be decreased. Accordingly, a polymer having a desired cloud point (e.g., a cloud point of higher than 30° C.), may be obtained by selecting monomers to be used for copolymerization.

Specific examples of the above hydrophilic monomers include: N-vinyl pyrrolidone, vinylpyridine, acrylamide, methacrylamide, N-methylacrylamide, hydroxyethylmethacrylate, hydroxyethylacrylate, hydroxymethylmethacrylate, hydroxymethylacrylate, methacrylic acid and acrylic acid having an acidic group, and salts of these acids, vinylsulfonic acid, styrenesulfonic acid, etc., and derivatives having a basic group such as N,N-dimethylaminoethylmethacrylate, N,N-diethylaminoethyl methacrylate, N,N-dimethylaminopropylacrylamide, salts of these derivatives, etc. However, the hydrophilic monomer to be usable in the present invention is not restricted to these specific examples.

On the other hand, specific examples of the above hydrophobic monomer may include acrylate derivatives and methacrylate derivatives such as ethylacrylate, methylmethacrylate, and glycidylmethacrylate; N-substituted alkymethacrylamide derivatives such as N-n-butylmethacrylamide; vinylchloride, acrylonitrile, styrene, vinyl acetate, etc. However, the hydrophobic monomer to be usable in the present invention is not restricted to these specific examples.

Figure 2A:
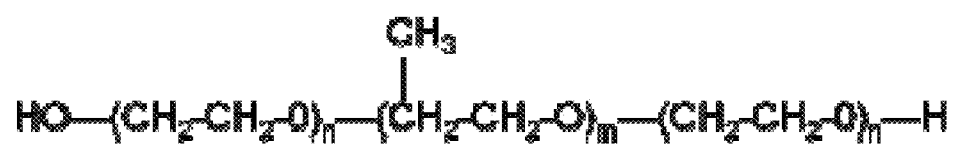
FIG. 2A shows the molecular structure.
Figure 2B:
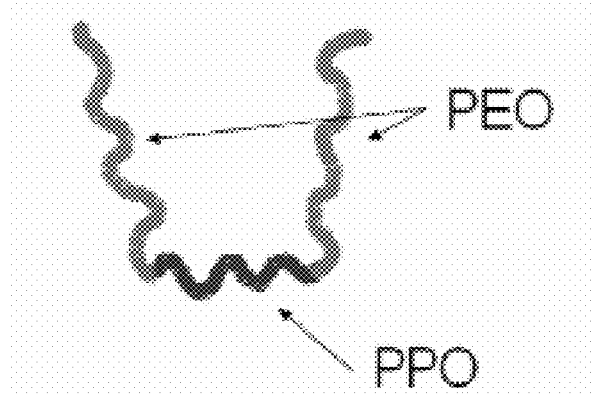
FIG. 2B is a schematic representation of the three-block polymeric chain.
Figure 3A:
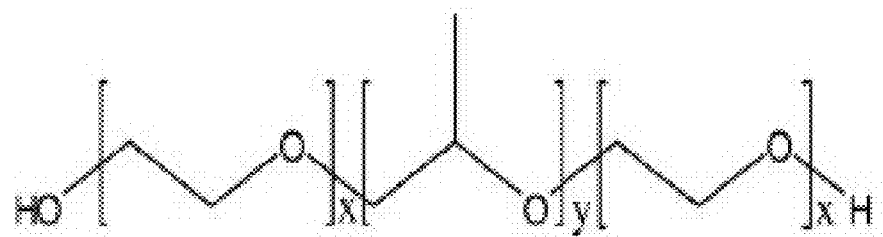
FIG. 3A shows the molecular structure.
Figure 3B:
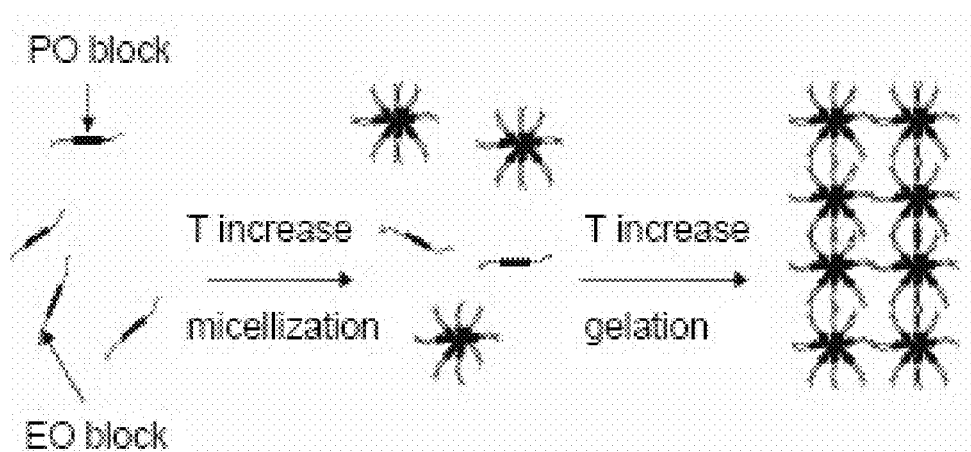
FIG. 3B is a schematic representation of the gelation process.

Among the polymers that show thermosensitive character is poly(ethylene oxide)-poly(propylene oxide)-poly(ethylene oxide) triblock copolymers (PEO-PPO-PEO) (Pluronics® or Poloxamers®) which is a family of ABA-type triblock copolymer consisting of more than 30 non-ionic amphiphilic copolymers (FIG. 2). The physical state (liquid, paste, solid) of these copolymers is governed by their MW and block ratio. Poloxamers are well tolerated (non-toxic) biocompatible polymer. These block copolymers show gelation at body temperature at concentrations greater than 15% (w/w). The above-described property of the blocks having a cloud point is caused by hydrophobic bond of the blocks whose strength increases with an increase in temperature and decreases with a decrease in temperature. In the present invention hydrophobic bonds form between the cloud point blocks replacing the bonds between the blocks and the water molecules, thereby causing the blocks to become insoluble. The presence of hydrophilic blocks imparts the polymer with the ability to form a water-containing gel rather than being precipitated at a temperature higher than the cloud point temperature due to an excess increase in the hydrophobic bonding strength of the cloud point blocks. The coexistence of the cloud point blocks and the hydrophilic blocks in the polymer causes it to be converted from a water-soluble sol state below the temperature into a water-insoluble gel state at a temperature at or above the cloud point temperature, which temperature essentially corresponds to the sol-gel transition temperature of the polymer (FIG. 3).

Figure 4A:
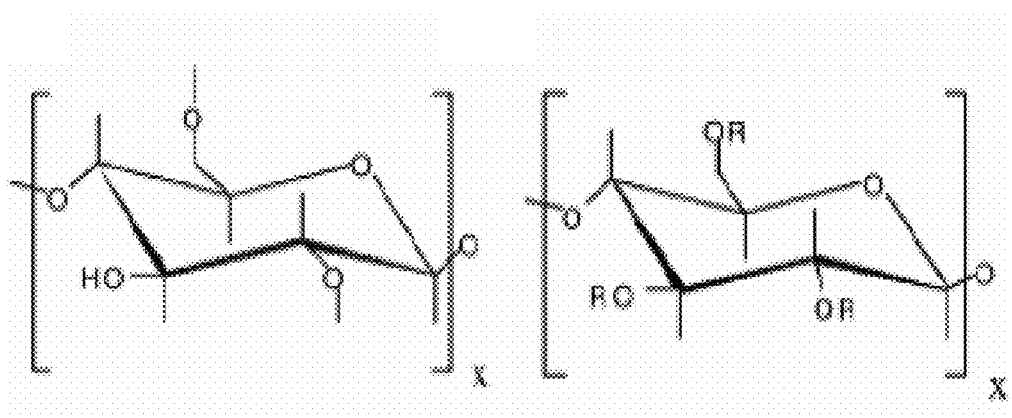
FIG. 4A shows the molecular structure.
Figure 4B:
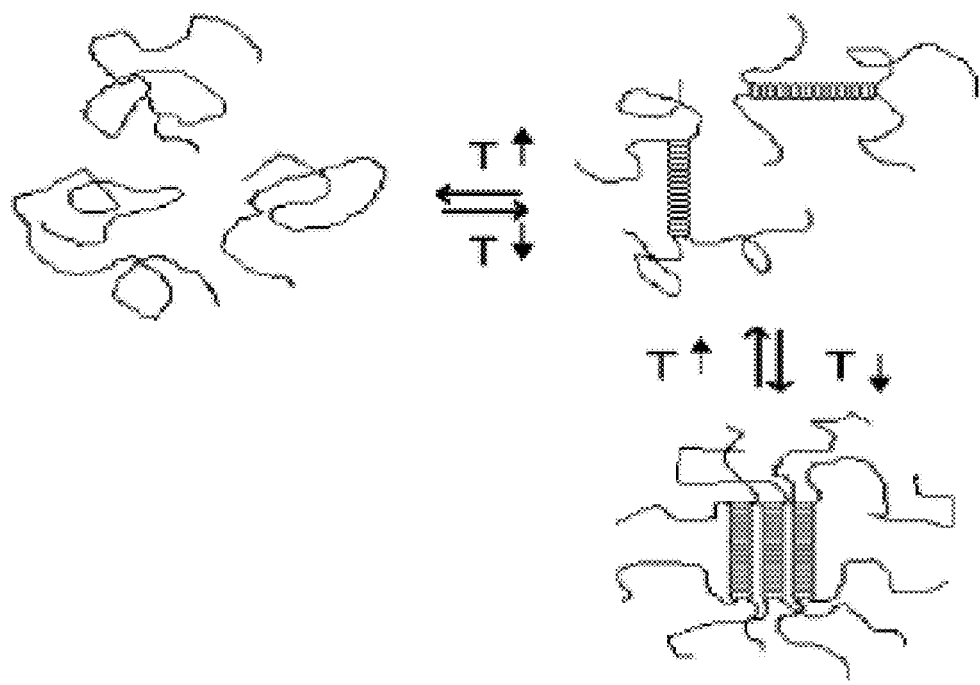
FIG. 4B is a schematic representation of the molecular interactions.
Figure 5:
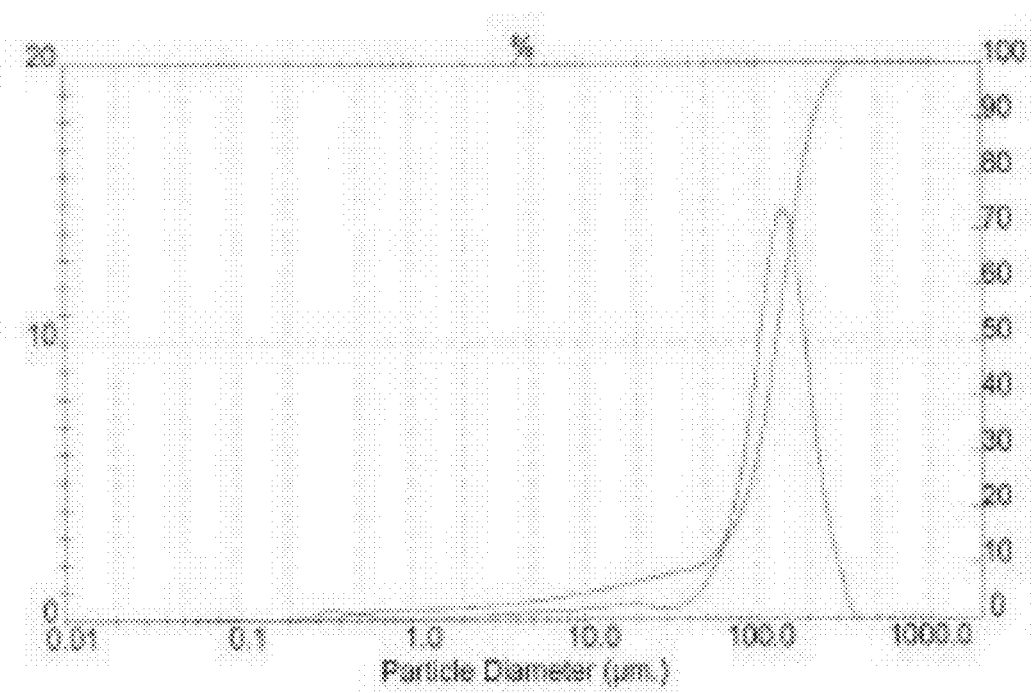
FIG. 5. is a graph of particle size distribution of microencapsulated *Bifidobacterium lactis* (BL818), made according to an embodiment of the invention described in Example 1, in water after heating at 70° C. and cooling down; hydroxypropyl cellulose (HPC LF) was used as thermo-sensitive sol-gel film coating with a weight gain of 70%.
Figure 6:
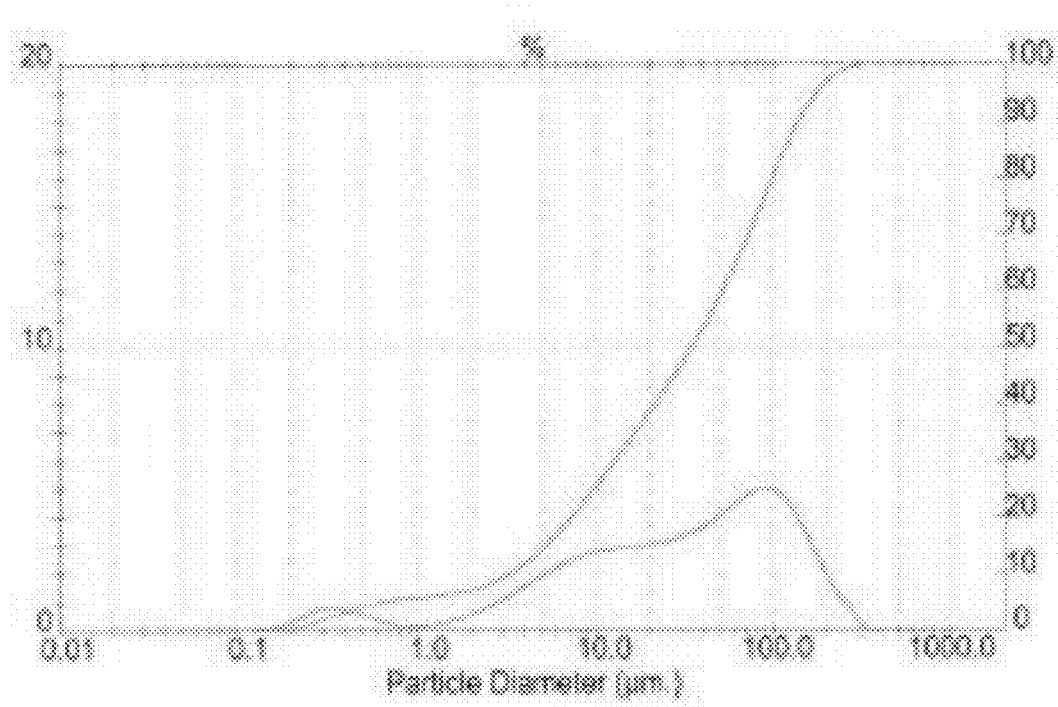
FIG. 6. is a graph of particle size distribution of microencapsulated *Bifidobacterium lactis* (BL818), in the form of stabilized granules according to the invention, in water after heating at 70° C. and cooling down; hydroxypropyl cellulose (HPC LF) was used as thermo-sensitive sol-gel film coating with a weight gain of 50%.
Figure 7:
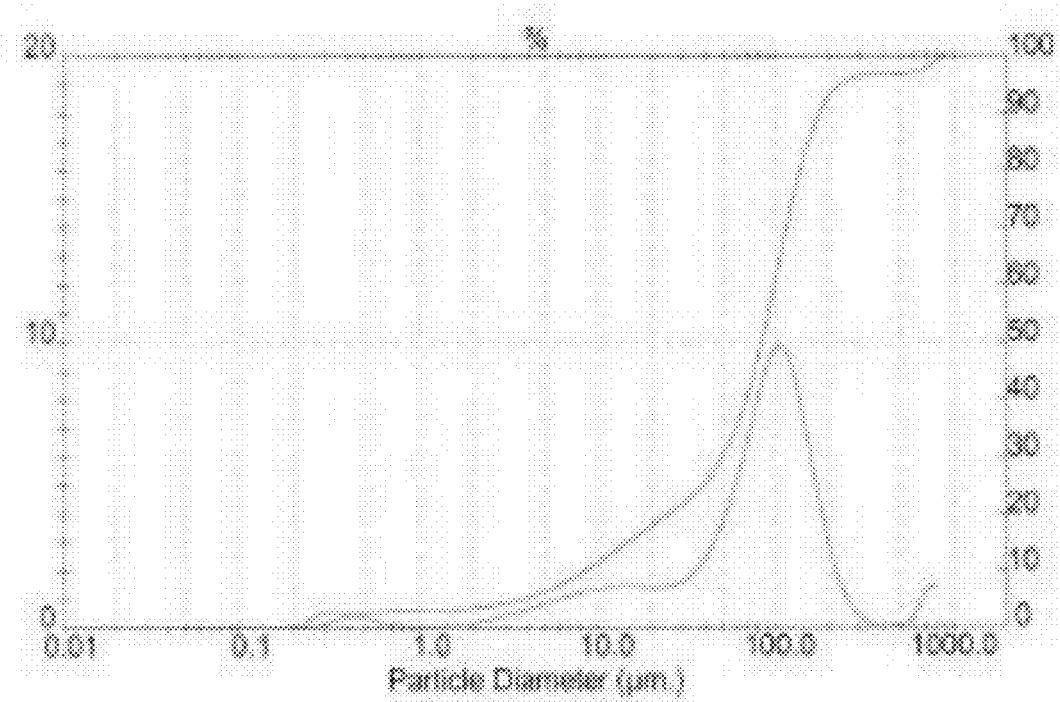
FIG. 7. is a graph of particle size distribution of microencapsulated *Bifidobacterium lactis* (BL818), made according to an embodiment of the invention described in Example 2, in water after heating at 70° C. and cooling down; hydroxypropyl cellulose (HPC EF) was used as thermo-sensitive sol-gel film coating with a weight gain of 70%

On the other hand, in the case of an etherified cellulose represented by methylcellulose, hydroxypropylcellulose, etc., the sol-gel transition temperature thereof is as high as about 45° C. or higher. Hydroxypropylcellulose (HPC) is an example of a thermo-sensitive polymer. HPC is an ether of cellulose in which some of the hydroxyl groups in the repeating glucose units have been hydroxypropylated forming —$OCH_2CH(OH)CH_3$ groups using propylene oxide. The average number of substituted hydroxyl groups per glucose unit is referred to as the degree of substitution (DS). Complete substitution would provide a DS of 3. Because the hydroxypropyl group added contains a hydroxyl group, this can also be etherified during preparation of HPC. When this occurs, the number of moles of hydroxypropyl groups per glucose ring, moles of substitution (MS), can be higher than 3. Since hydroxypropyl cellulose (HPC) has a combination of hydrophobic and hydrophilic groups, so it also has a lower critical solution temperature (LCST) at 45° C. At temperatures below the LCST, HPC is readily soluble in water; above the LCST, HPC is not soluble (FIG. 4).

The Exterior Coating Layer:

According to further features in any of the embodiments of the invention, the encapsulated probiotics optionally and preferably further comprises an outermost (exterior) coating layer which is preferably a water soluble polymer layer for enhancing the dissolution of said thermo-sensitive gel forming polymer on cooling below its cloud point or its lower critical solution temperature (LCST). Example of materials that may be used for the outermost coating layer is selected from the group consisting of water soluble or erodible polymers such as, for example, Povidone (PVP: polyvinyl pyrrolidone), Copovidone (copolymer of vinyl pyrrolidone and vinyl acetate), polyvinyl alcohol, Kollicoat Protect (BASF) which is a mixture of Kollicoat IR (a polyvinyl alcohol (PVA)-polyethylene glycol (PEG) graft copolymer) and polyvinyl alcohol (PVA), Opadry AMB (Colorcon) which is a mixture based on PVA, Aquarius MG which is a cellulose-based polymer containing natural wax, lecithin, xanthan gum and talc, low molecular weight HPC (hydroxypropyl cellulose), low molecular weight HPMC (hydroxypropyl methylcellulose) such as hydroxypropylcellulose (HPMC E3 or E5) (Colorcon), methyl cellulose (MC), low molecular weight carboxy methyl cellulose (CMC), low molecular weight carboxy methyl ethyl cellulose (CMEC), low molecular weight hydroxyethylcellulose (HEC), low molecular weight hydroxyl ethyl methyl cellulose (HEMC), low molecular weight hydroxymethylcellulose (HMC), low molecular weight hydroxymethyl hydroxyethylcellulose (HMHEC), low viscosity of ethyl cellulose, low molecular weight methyl ethyl cellulose (MEC), gelatin, hydrolyzed gelatin, polyethylene oxide, water soluble gums, water soluble polysaccharides, acacia, dextrin, starch, modified cellulose, water soluble polyacrylates, polyacrylic acid, polyhydroxyethylmethacrylate (PHEMA) and polymethacrylates and their copolymers, and/or a mixtures thereof.

Substrate:

According to a preferred embodiment of the invention, the probiotic bacteria in said granule core are mixed with a substrate. Said substrate preferably comprises at least one material that may be also a supplement agent for the probiotic bacteria. The substrate may comprise monosaccharides such as trioses including ketotriose (dihydroxyacetone) and aldotriose (glyceraldehyde), tetroses such as ketotetrose (erythrulose), aldotetroses (erythrose, threose) and ketopentose (ribulose, xylulose), pentoses such as aldopentose (ribose, arabinose, xylose, lyxose), deoxy sugar (deoxyribose) and ketohexose (psicose, fructose, sorbose, tagatose), hexoses such as aldohexose (allose, altrose, glucose, mannose, gulose, idose, galactose, talose), deoxy sugar (fucose, fuculose, rhamnose) and heptose such as (sedoheptulose), and octose and nonose (neuraminic acid). The substrate may comprise multiple saccharides such as 1) disaccharides, such as sucrose, lactose, maltose, trehalose, turanose, and cellobiose, 2) trisaccharides such as raffinose, melezitose and maltotriose, 3) tetrasaccharides such as acarbose and stachyose, 4) other oligosaccharides such as fructooligosaccharide (FOS), galactooligosaccharides (GOS) and mannan-oligosaccharides (MOS), 5) polysaccharides such as glucose-based polysaccharides/glucan including glycogen starch (amylose, amylopectin), cellulose, dextrin, dextran, beta-glucan (zymosan, lentinan, sizofiran), and maltodextrin, fructose-based polysaccharides/fructan including inulin, levan beta 2-6, mannose-based polysaccharides (mannan), galactose-based polysaccharides (galactan), and N-acetylglucosamine-based polysaccharides including chitin. Other polysaccharides may be comprised, including gums such as arabic gum (gum acacia).

According to preferred embodiments of the present invention, the core further comprises an antioxidant. Preferably, the antioxidant is selected from the group consisting of cysteine hydrochloride, cystein base, 4,4-(2,3 dimethyl tetramethylene dipyrocatechol), tocopherol-rich extract (natural vitamin E), α-tocopherol (synthetic Vitamin E), β-tocopherol, γ-tocopherol, δ-tocopherol, butylhydroxinon, butyl hydroxyanisole (BHA), butyl hydroxytoluene (BHT), propyl gallate, octyl gallate, dodecyl gallate, tertiary butylhydroquinone (TBHQ), fumaric acid, malic acid, ascorbic acid (Vitamin C), sodium ascorbate, calcium ascorbate, potassium ascorbate, ascorbyl palmitate, and ascorbyl stearate. Comprised in the core may be citric acid, sodium lactate, potassium lactate, calcium lactate, magnesium lactate, anoxomer, erythorbic acid, sodium erythorbate, erythorbin acid, sodium erythorbin, ethoxyquin, glycine, gum guaiac, sodium citrates (monosodium citrate, disodium citrate, trisodium citrate), potassium citrates (monopotassium citrate, tripotassium citrate), lecithin, polyphosphate, tartaric acid, sodium tartrates (monosodium tartrate, disodium tartrate), potassium tartrates (monopotassium tartrate, dipotassium tartrate), sodium potassium tartrate, phosphoric acid, sodium phosphates (monosodium phosphate, disodium phosphate, trisodium phosphate), potassium phosphates (monopotassium phosphate, dipotassium phosphate, tripotassium phosphate), calcium disodium ethylene diamine tetra-acetate (calcium disodium EDTA), lactic acid, trihydroxy butyrophenone and thiodipropionic acid and mixtures thereof. According to one preferred embodiment, the antioxidant is cystein base.

According to some embodiments of the present invention, the core further comprises both filler and binder. Examples of fillers include, for example, microcrystalline cellulose, a sugar, such as lactose, glucose, galactose, fructose, or sucrose; dicalcium phosphate; sugar alcohols such as sorbitol, manitol, mantitol, lactitol, xylitol, isomalt, erythritol, and hydrogenated starch hydrolysates; corn starch; potato starch; sodium carboxymethycellulose, ethylcellulose and cellulose acetate, or a mixture thereof. More preferably, the filler is lactose. Examples of binders include Povidone (PVP: polyvinyl pyrrolidone), Copovidone (copolymer of vinyl pyrrolidone and vinyl acetate), polyvinyl alcohol, low molecular weight HPC (hydroxypropyl cellulose), low molecular weight HPMC (hydroxypropyl methylcellulose), low molecular weight carboxy methyl cellulose, low molecular weight hydroxyethylcellulose, low molecular weight hydroxymethylcellulose, gelatin, hydrolyzed gelatin, polyethylene oxide, acacia, dextrin, starch, and water soluble polyacrylates and polymethacrylates, low molecular weight ethylcellulose or a mixture thereof.

Examples of probiotic bacteria include but are not limited to Bacillus coagulans GBI-30, 6086, Bacillus subtilis var natt, Bifidobacterium LAFTI® B94, Bifidobacterium sp LAFTI B94, Bifidobacterium bifidum, Bifidobacterium bifidum rosell-71, Bifidobacterium breve, Bifidobacterium breve Rosell-70, Bifidobacterium infantis, Bifidobacterium lactis, Bifidobacterium longum, Bifidobacterium longum Rosell-175, Bifidobacterium animalis, Bifidobacterium animalis subsp. lactis BB-12, Bifidobacterium animalis subsp. lactis HN019, Bifidobacterium infantis 35624, Escherichia coli M-17, Escherichia coli Nissle 1917, Lactobacillus acidophilus, Lactobacillus acidophilus LAFTI® L10, Lactobacillus acidophilus LAFTI L10, Lactobacillus casei LAFTI® L26, Lactobacillus casei LAFTI L26, Lactobacillus brevis, Lactobacillus bulgaricus, Lactobacillus casei, Lactobacillus gasseri, Lactobacillus paracasei, Lactobacillus plantarum, Lactobacillus reuteri ATTC 55730 (Lactobacillus reuteri SD2112), Lactobacillus rhamnosus, Lactobacillus salivarius, Lactobacillus delbrueckii, Lactobacillus fermentum, Lactococcus lactis, Lactococcus lactis subsp, Lactococcus lactis Rosell-1058, Lactobacillus paracasei St11 (or NCC2461) Lactobacillus fortis Nestlé, Lactobacillus johnsonii Lα1 (=Lactobacillus LC1, Lactobacillus johnsonii NCC533) Nestlé, Lactobacillus rhamnosus Rosell-11, Lactobacillus acidophilus Rosell-52, Streptococcus thermophilus, Diacetylactis, or other microorganisms like Saccharomyces cerevisiae, and a mixture thereof.

The processes described herein permit the manufacture of various healthy food products without separating the admixing and heating steps. For example and without limitation, the preparation of liquid-based products containing the probiotic granules directly mixed to the liquid, even before, during or shortly after a heating stage. The encapsulated probiotic bacteria according to the present invention may be incorporated into infant foods such as infant food powder compound, and/or liquid-based products that undergo heating steps during their manufacture or post-manufacture preparation. Without limitation, the encapsulated probiotic bacteria according to the present invention may be incorporated into products whose final transparency and appearance are an important marketing factor, as well as into hot drinks, into nectars and into fruit juices, and into other beverage products that may be exposed to higher than ambient temperature (room temperature) during their handling and/or production.

Various embodiments of the invention will be further described and illustrated in the following examples.

EXAMPLES

Example 1

Materials

| Materials: | Function: |
|---|---|
| Bifidobacterium lactis | A Probiotic bacteria |
| Maltodextrin | Core substrate |
| Trehalose | Core substrate |
| Hydroxypropyl starch | Core Binder |
| Hydroxypropyl starch | First coating layer agent |
| phosphated distarch phosphate | Second coating layer polymer |

Method

Hydroxypropyl starch (HPS) was dissolved in water at 90° C. for 20 minutes after which the polymer dissolved. Then a solution of HPS (5% w/w) in water was prepared.

Bifidobacterium lactis (BL 818)(44.8 g), maltodextrin (402.3 g) and trehalose (51.1 g) were granulated with the solution of HPS using an Innojet Ventilus coater machine. The resulting granules (518.9 g) were then coated using the above HPS solution by a sub-coating layer comprising (inner layer) HPS to obtain 10% (W/W) weight gain in the coated granule weight as compared to the weight of the core. The resulting coated granules were then coated with an outer coating comprising phosphated distarch phosphate using a 5% (W/W) solution in water/ethanol mixture to obtain 30% (W/W) weight gain in the coated granule weight as compared to the weight of the core plus the inner layer.

Example 2

Materials

| Materials: | Function: |
|---|---|
| Bifidobacterium lactis | A Probiotic bacteria |
| Maltodextrin | Core substrate |
| Trehalose | Core substrate |
| Hydroxypropyl starch | Core binder |
| Hydroxypropyl starch | First coating layer agent |
| acetylated distarch phosphate | Second coating layer polymer |

Method

Pre-gelatinized Hydroxypropyl starch (HPS) was dissolved in water at room temperature.

Bifidobacterium lactis (BL 818) (44.8 g), maltodextrin (402.3 g) and trehalose (51.1 g) were granulated with the solution of HPS using an Innojet Ventilus coater machine. The resulting granules (518.9 g) were then coated using the above HPS solution by a sub-coating layer comprising (inner layer) HPS to obtain 10% (W/W) weight gain in the coated granule weight as compared to the weight of the core. The resulting coated granules were then coated with an outer coating comprising acetylated distarch phosphate using a 5% (W/W) solution in water to obtain 30% (W/W) weight gain in the coated granule weight as compared to the weight of the core plus the inner layer.

Example 3

Heat Resistance Test Method in Solution of NaCl (0.9%) in Purified Water

Objective

Evaluation of the survival rate of microencapsulated bacteria according to the present invention. The test was done by dispersing the sample of microencapsulated bacteria particles in preheated NaCl solution (0.9%) in purified water at 70° C. for 5 minutes.

Principle of the Method

1. Sample of microencapsulated Probiotic particles are dispersed in water (NaCl solution, 0.9%) which preheated to 70° C.

2. After 5 minutes the water (NaCl solution 0.9%) is cooled down to below 40° C.

3. Microencapsulated probiotic particles is completely dissolved.

4. Enumeration test is performed to determine the colony forming units per gram of the bacteria content in the sample (CFU/g).

5. The results will be compared to those of blank samples (the bacteria without microencapsulation).

6. Control samples will be prepared by dissolution of both microencapsulated bacteria and the bacteria without microencapsulation directly in water (NaCl solution 0/9%) at room temperature (with no preheating).

Procedure for Heat Resistance Test Method

1. Weigh accurately 10 gram of the probiotic sample (either microencapsulated bacteria particles according to the present invention or the bacteria without microencapsulation).

2. Put 100 ml distilled water (NaCl solution 0.9%) in a glass beaker and heat to 70° C. using a bath equipped with a thermostat.

2. Measure and note the temperature.

3. Introduce the weighed sample into the water (NaCl solution 0.9%) and immediately start measuring time.

4. After 5 minutes accurately take out the glass beaker from the bath and cool down to 40° C.

5. Dissolve completely the sample of the microencapsulated bacteria particles using a shaker for about 0.25-4 hours depending on the weight gain of thermo-sensitive gel-forming coating layer.

6. Perform enumeration test and calculate CFU/gr.

Procedure for Control Sample

1. Weigh accurately 10 gram of the probiotic sample (either microencapsulated bacteria particles according to the present invention or the bacteria without microencapsulation).

2. Disperse the weighed sample into 100 ml water (NaCl solution 0.9%) at room temperature.

3. Dissolve completely the sample of the microencapsulated bacteria particles using a shaker for about 0.25-4 hours depending on the weight gain of thermo-sensitive gel-forming coating layer.
4. Perform enumeration test and calculate CFU/gr.

Example 4

Heat Resistance Test Method in Infant Milk

Formulation Suspension
Objective

Evaluation of the survival rate of microencapsulated bacteria according to the present invention. The test was done by dispersing the sample of microencapsulated bacteria particles in infant milk formulation suspension at 70° C. for 5 minutes.
Principle of the Method
1. Sample of microencapsulated Probiotic particles are dispersed in particles in infant milk formulation suspension at 70° C. for 5 minutes.
2. After 5 minutes infant milk formulation suspension is cooled down to below 40° C.
3. The infant milk formulation suspension is shaken to dissolve microencapsulated probiotic particles.
4. Enumeration test is performed to determine the colony forming units per gram of the bacteria content in the sample (CFU/g).
Procedure for Control Sample
1. Heat 210 ml of water to 70° C. and put into the flask.
2. Disperse mix powder of sample and infant milk powder into the flask.
3. Close the flask, turn vertical, shake 30× up and down.
4. Cool down milk, place the flask at room temperature until milk temperature is 37° C. (slow cooling); time estimation: 30 min.
5. Perform enumeration test and calculate CFU/gr.
Preparation of Mix Powder of Sample and Infant Milk Powder Mix powder I. 3.2 g of sample and 28.8 g of infant milk powder,
mix powder II. 9.6 g of sample and 22.4 g of infant milk powder,
mix powder III. 16 g of sample and 16 g of infant milk powder.

Example 5

Methods—Microencapsulation Process and Formulation

First, dried probiotic powder, maltodextrin were granulated with a solution of either hydroxypropylmethyl starch (HPS) (Tests 2, 3 and 5-8) or hydroxypropylmethyl cellulose (HPC) (Test 4) in purified water using an Innojet Ventilus coater machine. The resulting granules were then coated by the solution of either HPC (Test 4) or HPS or a combination of HPS and acetylated di-starch phosphate (ADSP) in purified water as described in the following table. The resulting microcapsules were then tested for a heat resistance test (survival test) in powdered infant formula (PIF) dispersion in purified water.

| Test | Batch # | Bacteria | Polymer Type | Bacteria content % (w/w) |
|---|---|---|---|---|
| 1 | BB pure as is | Bifidobacteria breve | | 100 |
| 2 | 13-0125-0134, 16.05.13 | Bifidobacteria breve | Two-layer microcapsules based on hydroxypropyl starch (HPS) 8% as an inner layer and Acetylated di-starch phosphate (ADSP) 23% as an outer layer | 6.18 |
| 3 | 13-0129-0134_D | Bifidobacteria breve | One-layer microcapsules based on hydroxypropyl starch (HPS) 37% | 5.6 |
| 4 | 13-0130-0134_B | Bifidobacteria breve | One-layer microcapsules based on hydroxypropyl cellulose (HPC) 37% | 5.6 |
| 5 | 13-0171-0134_D2, | Bifidobacteria breve | Two-layer microcapsules based on hydroxypropyl starch (HPS) 19% as an inner layer and Acetylated di-starch phosphate (ADSP) 19% as an outer layer | 6.25 |
| 6 | 13-0185-0134_C | Bifidobacteria breve | One-layer microcapsules based on hydroxypropyl starch (HPS) and acetylated di-starch phosphate (ADSP) (1:1 weight ratio) 37% | 30.83 |
| 7 | 13-0359-0134+_B | Bifidobacteria breve | One-layer microcapsules based on hydroxypropyl starch (HPS) and acetylated di-starch phosphate (ADSP) (7:3 weight ratio) 9-26% | 36.1 |
| 8 | 13-0387-0134+_B | Bifidobacteria breve | One-layer microcapsules based on hydroxypropyl starch (HPS) and acetylated di-starch phosphate (ADSP) (7:3 weight ratio) 9-26% | 43.3 |

Survival Testing Method in Powdered Infant Formula (PIF) Dispersion

The test method for the survival rate of *B. Breve* in PIF was adapted from the new guidelines issued by WHO in collaboration with FAO of the United Nations (World Health Organization. Safe Preparation, Storage and Handling of Powdered Infant Formula. Guidelines 2007). Generally, the test was conducted by dispersing a prior prepared mixture of the samples of microencapsulated bacteria particles with the PIF in a certain volume of purified preheated water at different temperature in a plastic baby bottle. The bottle was then capped and shaken constantly and continuously up and down for different periods of time. Then the PIF dispersion was cooled down to 37° C., by allowing it to stay at room temperature. An enumeration test was then performed on the entire volume of the dispersion to determine the CFU of the bacteria in the PIF dispersion.

Results of Tests 1-6

The results of enumeration test of different microencapsulation formulations as compared to *B. breve* as is (non-microencapsulated), are presented in the following table.

| Test | Test item | Temperature test ° C. | CFU/bacteria 3 min | CFU/bacteria 5 min |
|---|---|---|---|---|
| 2 | 13-0125-0134 | 40 | $6.3 \times 10^9$ | $3.1 \times 10^9$ |
| | | 70 | $3.4 \times 10^6$ | $1.1 \times 10^6$ |
| | | 85 | $3.4 \times 10^6$ | $4.7 \times 10^5$ |
| | | 100 | $3.4 \times 10^4$ | $3.4 \times 10^4$ |
| 3 | 13-0129-134 D | 40 | $4.5 \times 10^9$ | $6.0 \times 10^9$ |
| | | 70 | $3.2 \times 10^7$ | $5.1 \times 10^7$ |
| | | 85 | $2.1 \times 10^7$ | $6.4 \times 10^7$ |
| | | 100 | $1.7 \times 10^7$ | $4.1 \times 10^4$ |
| 4 | 13-0130-134_B | 40 | $2.5 \times 10^{10}$ | $2.5 \times 10^{10}$ |
| | | 70 | $1.7 \times 10^7$ | $5.3 \times 10^7$ |
| | | 85 | $<4.1 \times 10^4$ | $4.1 \times 10^6$ |
| | | 100 | $2.3 \times 10^6$ | $8.2 \times 10^4$ |
| 5 | 13-0171-0134_D2 | 40 | $6.4 \times 10^8$ | $1.2 \times 10^9$ |
| | | 70 | $1.1 \times 10^7$ | $1.8 \times 10^7$ |
| | | 85 | $<1 \times 10^5$ | $<1 \times 10^5$ |
| | | 100 | $<1 \times 10^5$ | $<1 \times 10^5$ |
| 6 | 13-0185-0134_C | 40 | $3.4 \times 10^9$ | $7.8 \times 10^9$ |
| | | 70 | $4.9 \times 10^7$ | $3.9 \times 10^7$ |
| | | 85 | $<1 \times 10^5$ | $<1 \times 10^5$ |
| | | 100 | $<1 \times 10^5$ | $<1 \times 10^5$ |
| 1 | Bifidobacteria breve | 40 | $>10^{10}$ | $>10^{10}$ |
| | | 70 | $7.3 \times 10^5$ | $7.8 \times 10^5$ |
| | | 85 | $<1 \times 10^4$ | $<1 \times 10^4$ |
| | | 100 | $<1 \times 10^4$ | $<1 \times 10^4$ |

Results of Tests 7 and 8

The results of CFU/g bacteria at both 40° C. and 70° C. (in Aptamil for 5 minutes) for both bathes having different coating layer thicknesses are summarized in the following tables.

| Test 7 (Batch # 13-0359-0134+_B) | | | |
|---|---|---|---|
| Sample | Coating weight gain (%) | 40° C. CFU/g bacteria | 70° C. CFU/g bacteria |
| BB | B. breve pure as is | $3.5 \times 10^{10}$ | $2.3 \times 10^4$ |
| 1 | Core (uncoated) | $7.2 \times 10^{10}$ | ND |
| 2 | 10 | $1.9 \times 10^{10}$ | $1.7 \times 10^5$ |
| 3 | 20 | $4.2 \times 10^9$ | $9.6 \times 10^6$ |
| 4 | 30 | $4.8 \times 10^9$ | $1.5 \times 10^8$ |
| 5 | 35 | $3.3 \times 10^9$ | $5.8 \times 10^6$ |

ND—Not determined

| Test 8 (Batch # 13-0387-0134+_B) | | | |
|---|---|---|---|
| Sample | Coating weight gain (%) | 40° C. CFU/g bacteria | 70° C. CFU/g bacteria |
| BB | B. breve pure as is | $3.5 \times 10^{10}$ | $2.3 \times 10^4$ |
| 1 | Core (uncoated) | $8.2 \times 10^{10}$ | $6.0 \times 10^5$ |
| 2 | 10 | $3.0 \times 10^{10}$ | $4.9 \times 10^6$ |
| 3 | 20 | $1.1 \times 10^9$ | $2.7 \times 10^7$ |
| 4 | 30 | $9.8 \times 10^9$ | $8.7 \times 10^6$ |
| 5 | 35 | $5.3 \times 10^9$ | $6.0 \times 10^6$ |

While this invention has been described in terms of some specific examples, many modifications and variations are possible. It is therefore understood that within the scope of the appended claims, the invention may be realized otherwise than as specifically described.

The invention claimed is:

1. A composition for the preparation of heat and humidity resisting probiotic bacteria in the form of stabilized probiotic granules for an infant food product, comprising:
   i) core granules containing probiotic bacteria, at least one substrate, and optionally other food grade ingredients;
   ii) at least one inner layer comprising a starch based polymer coating said core granules, and protects the probiotic bacteria by forming a viscous gel upon contact with an aqueous solution wherein dissolution occurs after at least 30 seconds, 1 minute, 2 minutes, 3 minutes, 4 minutes, or 5 minutes; and
   wherein the starch based polymer comprises a component selected from the group consisting of native starch, thermoplastic starch, modified starch, partially pre-gelatinized starch and pre-gelatinized starch; carrageenan, guar gum and carob bean gum (also known as locust bean gum); or a combination thereof;
   iii) an outer layer comprising a thermo-reversible (thermo-sensitive) sol-gel forming polymer; and
   wherein the outer layer becomes viscous gel at 70° C., while the inner layer is soluble at 70° C.

2. The composition of claim 1, wherein the modified starch comprises one or more of Acid-treated starch (E1401), Alkaline-treated starch (E1402), Bleached starch (E1403), Oxidized starch (E1404), Starches, enzyme-treated (E1405), Monostarch phosphate (E1410), Distarch glycerol (E1411), Distarch phosphate esterified with sodium trimetaphosphate (E1412), Phosphated distarch phosphate (E1413), Acetylated distarch phosphate (E1414), Starch acetate esterified with acetic anhydride (E1420), Starch acetate esterified with vinyl acetate (E1421), Acetylated distarch adipate (E1422), Acetylated distarch glycerol (E1423), Hydroxypropyl starch (E1440), Hydroxypropyl distarch phosphate (E1442), Hydroxypropyl distarch glycerol (E1443), and Starch sodium octenyl succinate (E1450).

3. The composition of claim 1, wherein the starch based polymer is selected from the group consisting of hydroxypropyl starch, phosphated distarch phosphate and acetylated distarch phosphate.

4. The composition of claim 1, wherein, there is a difference of at least 5° C., at least 10° C., at least 15° C., at least 20° C., at least 25° C., or at least 30° C. between temperatures at which the inner and outer layers become soluble.

5. The composition of claim 1, wherein at each temperature at which the inner layer or outer layer layer becomes soluble, dissolution occurs after at least 30 seconds, 1 minute, 2 minutes, 3 minutes, 4 minutes or 5 minutes.

6. The composition of claim 5, wherein dissolution occurs in two stages: an initial gel forming stage and a stage of dispersal of said gel, and wherein said seconds or minutes relate to elapsed time for occurrence of both stages.

7. The composition of claim 4, wherein the inner and outer layer protect the probiotic bacteria at 70° C. in an aqueous media for at least 30 seconds by forming a viscous gel.

8. The composition of claim 7, wherein the outer layer dissolves in an aqueous media at 70° C. after at least 30 seconds, 1 minute, 2 minutes, 3 minutes, 4 minutes or 5 minutes.

9. The composition of claim 8, wherein the outer layer comprises phosphated distarch phosphate, acetylated distarch phosphate or a combination thereof.

10. The composition of claim 1, wherein said infant food product is an infant formula in a liquid concentrate state, powdered state or ready-to-use state.

11. A composition for the preparation of heat and humidity resisting probiotic bacteria in the form of stabilized probiotic granules for an infant food product, comprising:
  i) core granules containing probiotic bacteria, at least one substrate, and optionally other food grade ingredients;
  ii) an inner layer coating the core comprising hydroxypropyl starch; and
  iii) an outer layer comprising phosphated distarch phosphate, acetylated distarch phosphate or a combination thereof.

* * * * *